(12) United States Patent
Chang (10) Patent No.: US 7,219,667 B2
(45) Date of Patent: *May 22, 2007

(54) HAND PRESS TYPE RAPID POSITIONING FIRST-AID DEVICE WITH CARDIOPULMONARY RESUSCITATION

(76) Inventor: Tien-Tsai Chang, 5F, 28 Kuo-Hsiao Road, Hsin-Tien City, Taipei Hsien (TW)

( * ) Notice: Subject to any disclaimer, the term of this patent is extended or adjusted under 35 U.S.C. 154(b) by 146 days.

This patent is subject to a terminal disclaimer.

(21) Appl. No.: 11/014,167

(22) Filed: Dec. 17, 2004

(65) Prior Publication Data

US 2006/0130831 A1    Jun. 22, 2006

(51) Int. Cl.
*A61M 1/00* (2006.01)
*A62B 7/00* (2006.01)
*A62B 18/00* (2006.01)

(52) U.S. Cl. ............... 128/204.18; 128/205.18
(58) Field of Classification Search ........... 128/204.18, 128/205.18; 600/16
See application file for complete search history.

(56) References Cited

U.S. PATENT DOCUMENTS

| | | | | |
|---|---|---|---|---|
| 4,198,963 A | * | 4/1980 | Barkalow et al. | 601/106 |
| 4,338,924 A | * | 7/1982 | Bloom | 601/41 |
| 4,349,015 A | * | 9/1982 | Alferness | 601/41 |
| 4,915,095 A | * | 4/1990 | Chun | 601/43 |
| 5,295,481 A | * | 3/1994 | Geeham | 601/43 |
| 5,634,886 A | * | 6/1997 | Bennett | 601/41 |
| 5,823,185 A | * | 10/1998 | Chang | 128/204.18 |
| 5,931,850 A | * | 8/1999 | Zadini et al. | 606/192 |
| 5,979,444 A | * | 11/1999 | Sherrod | 128/205.25 |
| 6,296,653 B1 | * | 10/2001 | Zadini et al. | 606/192 |
| 6,397,843 B1 | * | 6/2002 | Tien-Tsai | 128/204.18 |
| 7,032,596 B2 | * | 4/2006 | Thompson et al. | 128/205.13 |
| 2003/0178025 A1 | * | 9/2003 | Holt et al. | 128/205.13 |
| 2005/0217675 A1 | * | 10/2005 | Thompson et al. | 128/205.13 |
| 2006/0180146 A1 | * | 8/2006 | Thompson et al. | 128/202.28 |

* cited by examiner

*Primary Examiner*—Patricia Bianco
*Assistant Examiner*—Kiandra C Lewis
(74) *Attorney, Agent, or Firm*—Troxell Law Office, PLLC (57) ABSTRACT

A hand press type rapid positioning first-aid device with cardiopulmonary resuscitation comprises a press device, an air storage device, a control device, a binding device and a sucking disc. The binding device allows the first-aid device being secured to the chest of the patient rapidly and conveniently. An operation process of continuously pressing the pressed part of the patient five times and blowing air one time after the mouth and nose breather masking the mouth and nose of the patient makes the first-aid cardiopulmonary resuscitation more successful and easily to enhance the function of first-aid. The disposal part, which contacts with the patient, in the mouth and nose breather can prevent from possible bacteria infection between patients.

15 Claims, 10 Drawing Sheets

FIG. 12

HAND PRESS TYPE RAPID POSITIONING FIRST-AID DEVICE WITH CARDIOPULMONARY RESUSCITATION

BACKGROUND OF THE INVENTION

1. Field of the Invention

The present invention is related to a first-aid cardiopulmonary resuscitation and particularly to a hand press type first-aid device with cardiopulmonary resuscitation.

2. Brief Description of Related Art

U.S. Pat. No. 5,823,185, which has been granted to the present inventor, discloses a manual pressing and automatic air breathing cardiopulmonary resuscitation first-aid device as shown in FIG. 1 comprises a manual pressing shaft 1', a pump 2', an air storage tank under the pump 2', a frame 4', a height-adjustable stand 5', an air control valve 6', a sucking disk 7', a mouth-nose breather 8' and an air passage pipe 9'.

Figure 1:
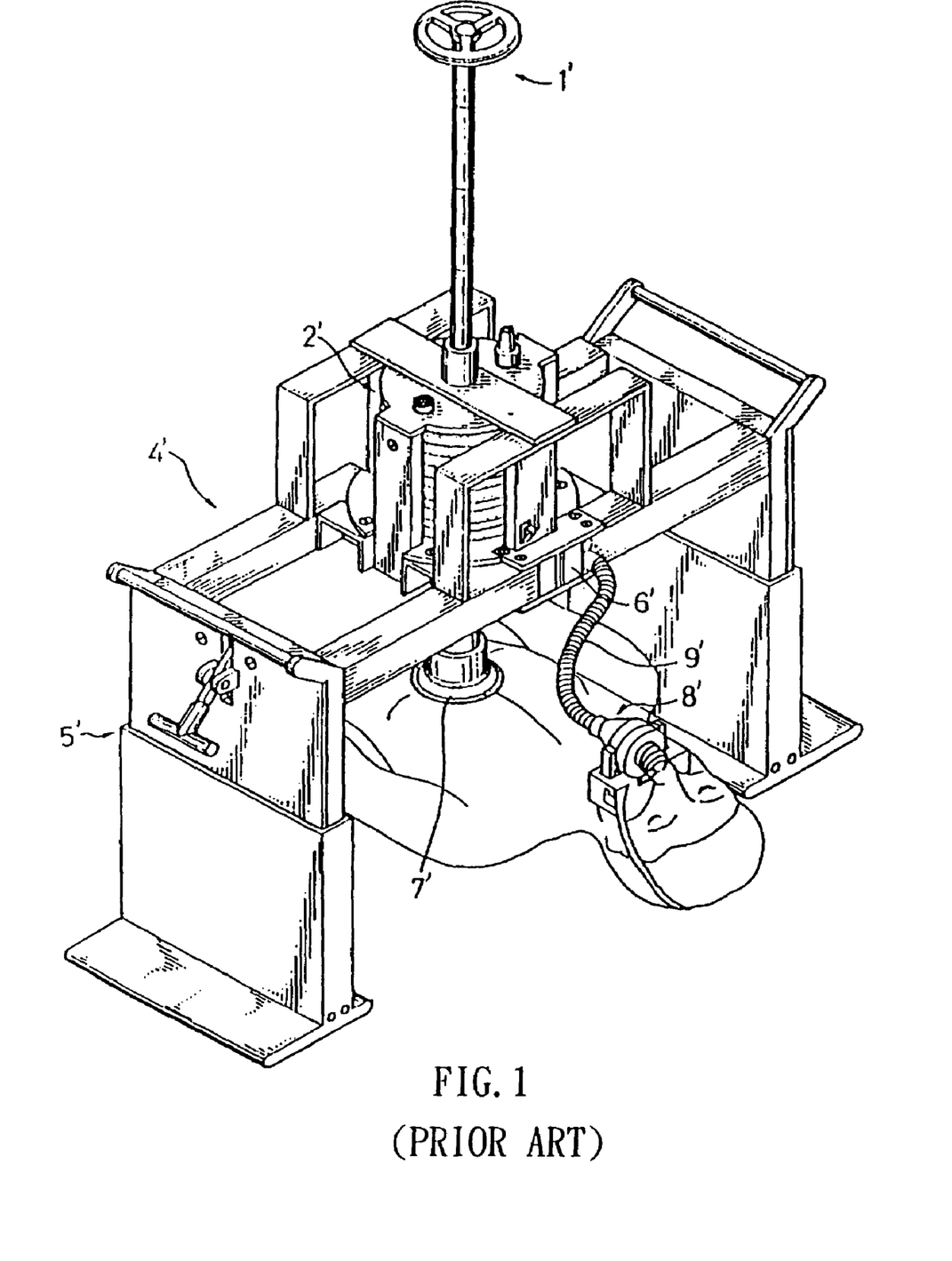
FIG. 1 is FIG. 1 of U.S. Pat. No. 5,823,185.
Figure 2:
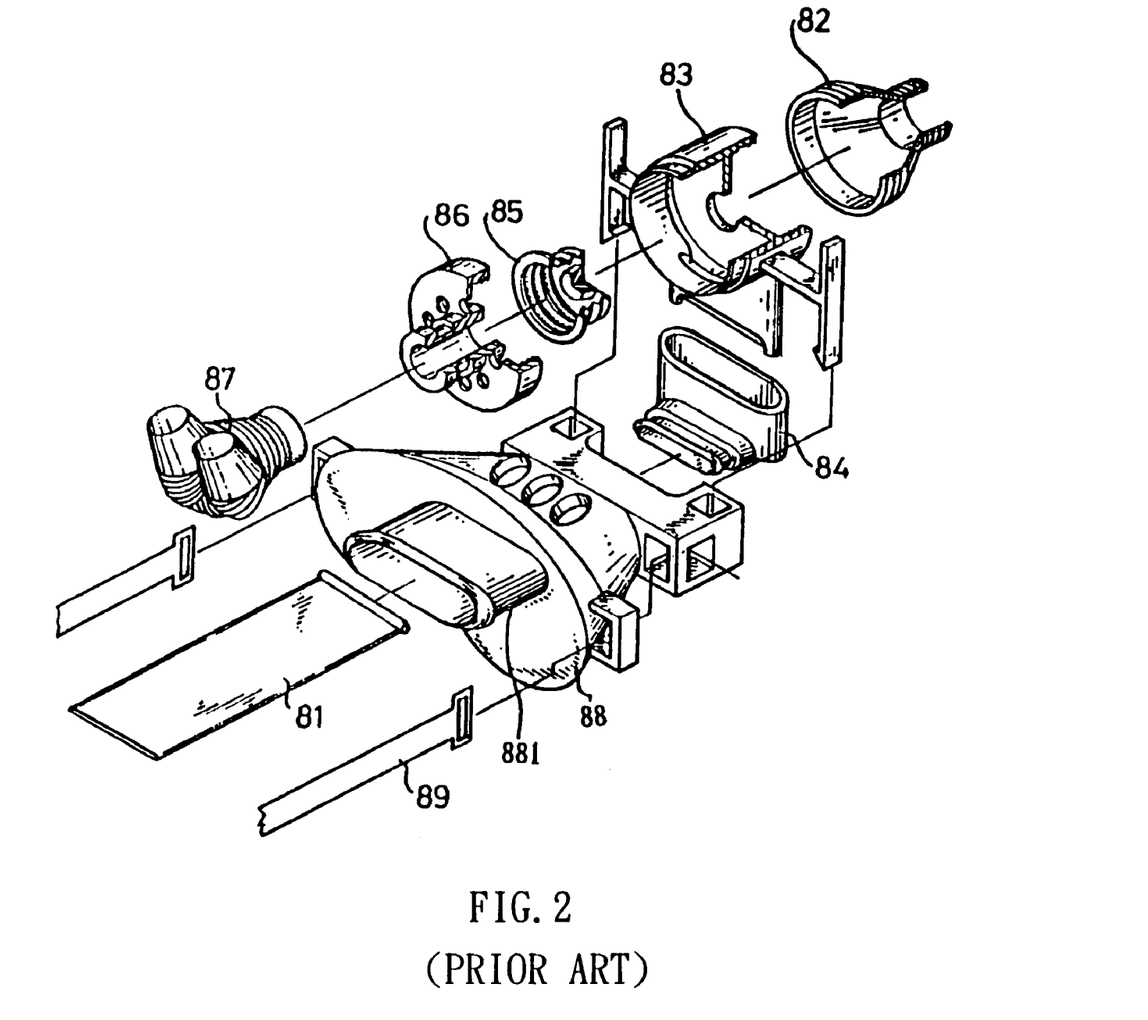
FIG. 2 is FIG. 7 of U.S. Pat. No. 5,823,185.
Figure 3:
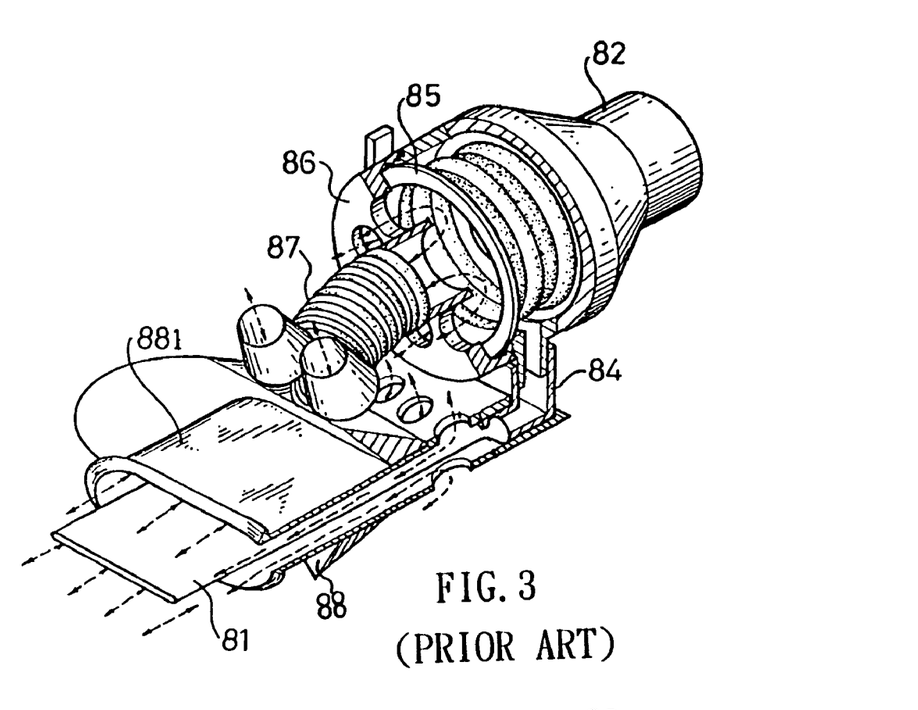
FIG. 3 is FIG. 8 of U.S. Pat. No. 5,823,185.
Figure 4:
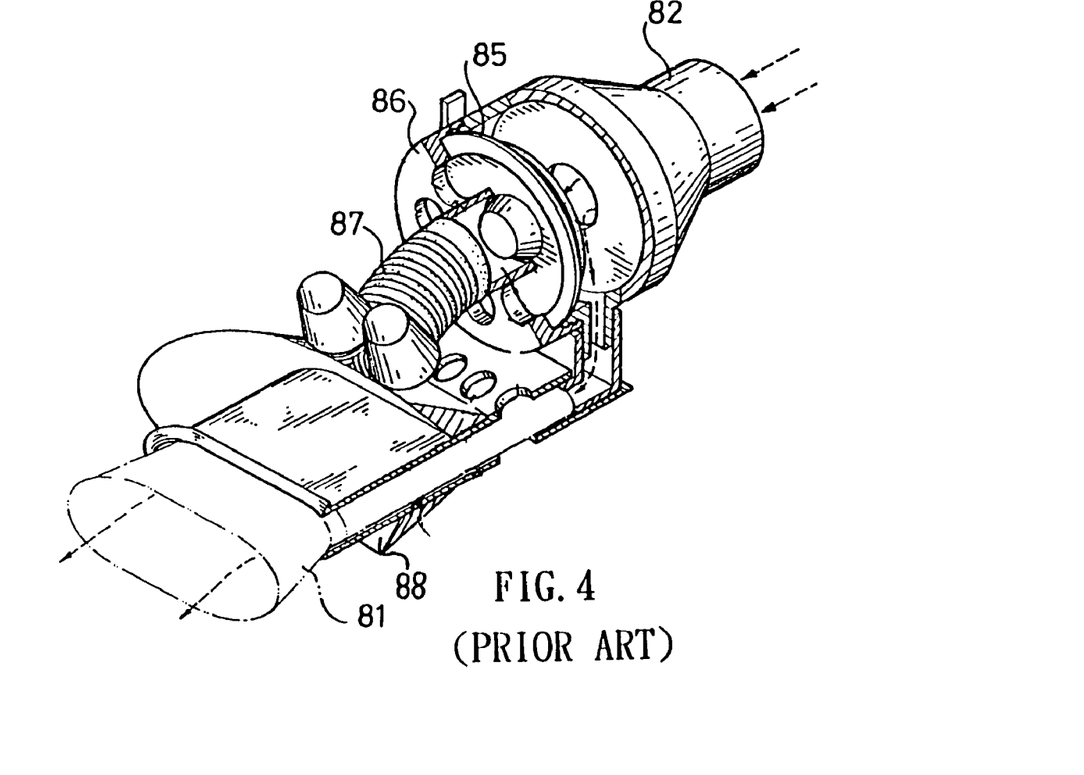
FIG. 4 is FIG. 9 of U.S. Pat. No. 5,823,185.

Referring to FIG. 2 to FIG. 4 in company with FIG. 1, the mouth-nose breather 8' is used to be attached to the mouth and nose of a patient and is composed of a hose 81, a coupling sleeve 82, an air-turning baffler 83, a sleeve 84, a two-way valve 85, a nostril breather 86, a nostril three-way pipe 87, a hollow mask 88, a mouth holder 881 and a Hook and loop belt 89. An end of an air duct 9' connects with the air control valve 6' and the air-turning baffle 83 is connected to another end of the air duct 9'. The two-way valve 85 has a shape of post, which is made of elastic material and received in the air-turning baffler 83, has a conical shape. The nostril breather 86 has a central air guide pipe and a plurality of apertures at the periphery thereof with a side thereof facing the air-turning baffle 83. The nostril three-way pipe 87 provides two holes at an end thereof to communicate with the nose of the patient and has a single hole at another end thereof for communicating with the air guide pipe of the nostril breather 86. The sleeve 84 connects with the air-turning baffler 83 at an end thereof and connects with the mouth holder 881. Another end of the mouth holder 881 is placed at the inner side of the mouth. An end of the hose 81 is inserted into the mouth and joined to the mouth holder 881 and another end of the hose 81 is connected to the air turning baffler 83. The hollow mask 88 provides a shape accommodating with the mouth for preventing the mouth holder 881 or the hose from being inserted too deep into the mouth.

The preceding cardiopulmonary resuscitation first-aid device can blow air one time after pressing patient five times to urge the patient reviving as soon as possible. The mouth and nose of the helper do not have to touch the patient to avoid being infected.

Figure 5:
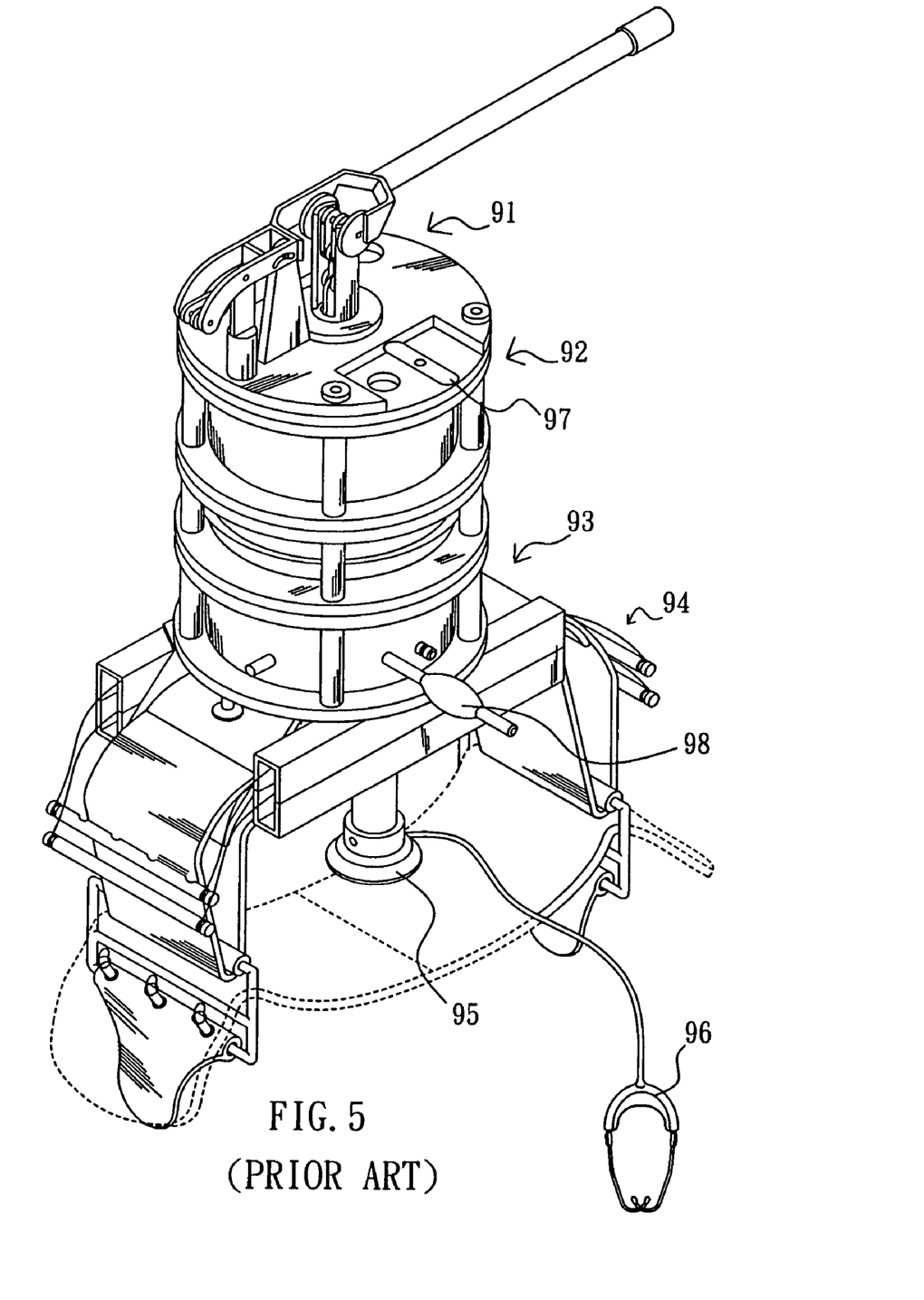
FIG. 5 is FIG. 1 of U.S. Pat. No. 6,397,843.

Referring to FIG. 5, U.S. Pat. No. 6,397,843, which is owned by the inventor too, discloses an electrical and manual pressing device of automated air blowing for first-aid cardiopulmonary resuscitation. The Electrical and manual pressing device of automated air blowing for first-aid cardiopulmonary resuscitation comprises a press unit 91, a storage unit 92, a control unit 93, a tying unit 94, a stucking disk 95 and a stethoscope 96. U.S. Pat. No. 6,397,843 provides functions such as the air being able to be filled by way of electrical actuation or manual pressing, offering a great deal of air, maintaining a constant pressing force against the heart, quickly fixing the sucking disk at a proper pressing position based on the size of the patient' body, quickly checking a breathing reaction of the patient by way of the air level, checking the heart beat by way of the stethoscope, mixing the oxygen with the air through the air mixing chamber in the air control valve, supplementing the oxygen or the fresh air after the heat beat restoring by way of the pumping ball, and etc.

SUMMARY OF THE INVENTION

An object of the present invention is to provide a hand press type rapid positioning first-aid device with cardiopulmonary resuscitation, which can be joined to the chest of the patient fast and conveniently.

Another object of the present invention is to provide a hand press type rapid positioning first-aid device with cardiopulmonary resuscitation, which has a simple structure for being fabricated easily.

A further object of the present invention is to provide a hand press type rapid positioning first-aid device with cardiopulmonary resuscitation, which has more filled air amount to supply sufficient blown air.

BRIEF DESCRIPTION OF THE DRAWINGS

The present invention can be more fully understood by reference to the following description and accompanying drawings, in which.

DETAILED DESCRIPTION OF THE INVENTION

Figure 6:
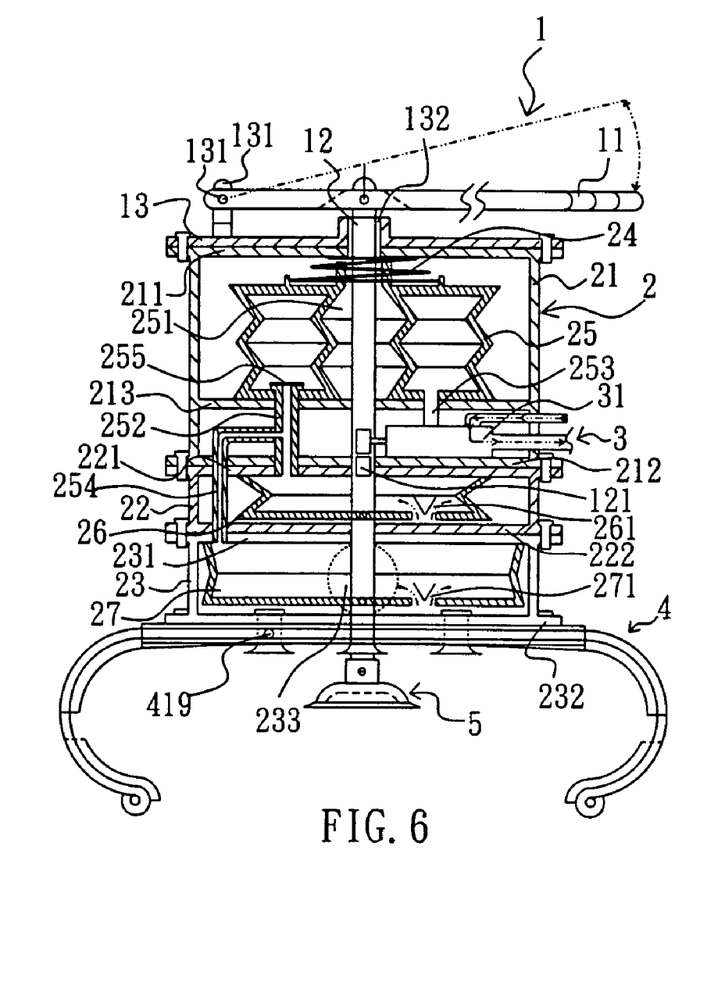
FIG. 6 is a sectional view with fragmentary side view illustrating the air storage device of the present invention filling in air.
Figure 11:
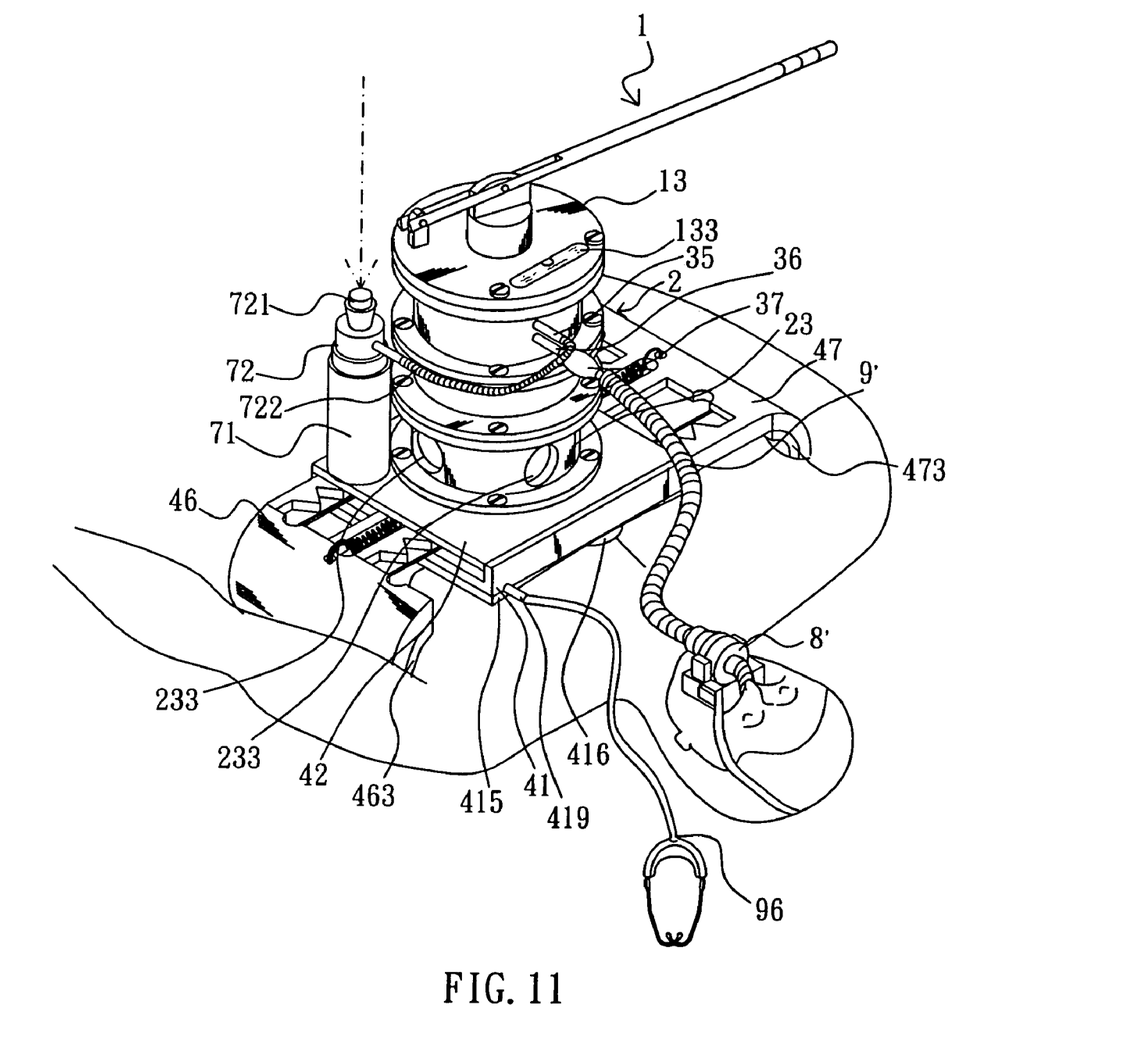
FIG. 11 is a perspective view illustrating hand press type rapid positioning first-aid device with cardiopulmonary resuscitation according to the present invention.

Referring to FIGS. 6 and 11, a hand press type rapid positioning first-aid device with cardiopulmonary resuscitation according to the present invention comprises a pressing device 1, an air storage device 2, a control device 3, a tying device 4 and a sucking disc 5.

The pressing device 1 includes a hand-press lever 11, which movably connects with the top end of an actuating rod 12. A fixing plate 13 provides a fulcrum stem 131 and a central through hole 132 for being passed through with the actuating rod 12. The hand-press lever 11 pivotally connects with the fulcrum stem 131 at an end thereof and can move upward and downward freely at another end thereof to drive the actuating rod 12 to move upward and downward. The actuating rod 12 has a push piece 121 jutting out from the outer wall surface of the actuating rod 12. A sucking disc 5 is attached to the lower end of the actuating rod 12.

The air storage device includes a first cylindrical member 21, a second cylindrical member 22 and a third cylindrical member 23, which are joined to each other sequentially. The three cylindrical members 21, 22, 23 provide a hole at top plates 211, 221, 231 and bottom plates 212, 222, 232 thereof respectively for being penetrated with the actuating rod 12. The first cylindrical member 21 further provides a partition 213 between the top plate 211 and the bottom plate 212 thereof. The partition 213 has a hole for being penetrated with the actuating rod 12 too. The top plate 211 of the first cylindrical member 21 is attached to the bottom side of the fixing plate 13. A compression spring 24 and a first extendable air pump 25 are mounted in the first cylindrical member 21. Both ends of the compression spring 24 are joined to the top plate 211 and the upper end of the first extendable air pump 25 respectively. The lower end of the first extendable air pump 25 is joined to the partition 213. A central hole 251 of the first extendable air pump 25 can be penetrated with the actuating rod 12. The first extendable air pump 25 and the partition 213 have a a hole respectively to be air-tightly joined to a first intake pipe 252 and a first discharge pipe 253. A bubble level gage 133 is attached to the top of the fixing plate 13 as shown in FIG. 11.

A second extendable air pump 26 and a third extendable air pump 27 are disposed in the second cylindrical member 22 and the third cylindrical member 23 to joined to the top plates 221, 231 respectively. The second extendable air pump 26 and the third extendable air pump 27 provide a hole respectively to be penetrated with the actuating rod 12 and have the bottoms thereof being joined to the outer wall surface of the actuating rod 12 air-tightly so that both the extendable air pumps 26, 27 can be driven with the actuating rod 12 to perform an extended movement respectively. The second extendable air pump 26 and the third extendable air pumps 27 provide a unidirectional valve 261, 271 at the lower ends thereof respectively. The bottom plate 212 of the first cylindrical member 21 has a hole corresponding to a hole at the top plate 221 of the second cylindrical member 22 to connect with the lower end of the first intake pipe 252 air-tightly and connect with the second intake pipe 254 first cylindrical member 21. The bottom plate 222 of the second cylindrical member 22 and the top plate 231 of the third cylindrical member 21 provide a hole respectively to correspond to each other for connecting with the lower end of the second intake pipe 254 air-tightly. The upper end of the second intake pipe 254 is joined to the first intake pipe 252 to communicate with each other. The upper end of the first intake pipe 252 is attached with a unidirectional valve 255. The third cylindrical member 23 provides an observation hole 233 at the cylindrical wall thereof.

Figure 7:
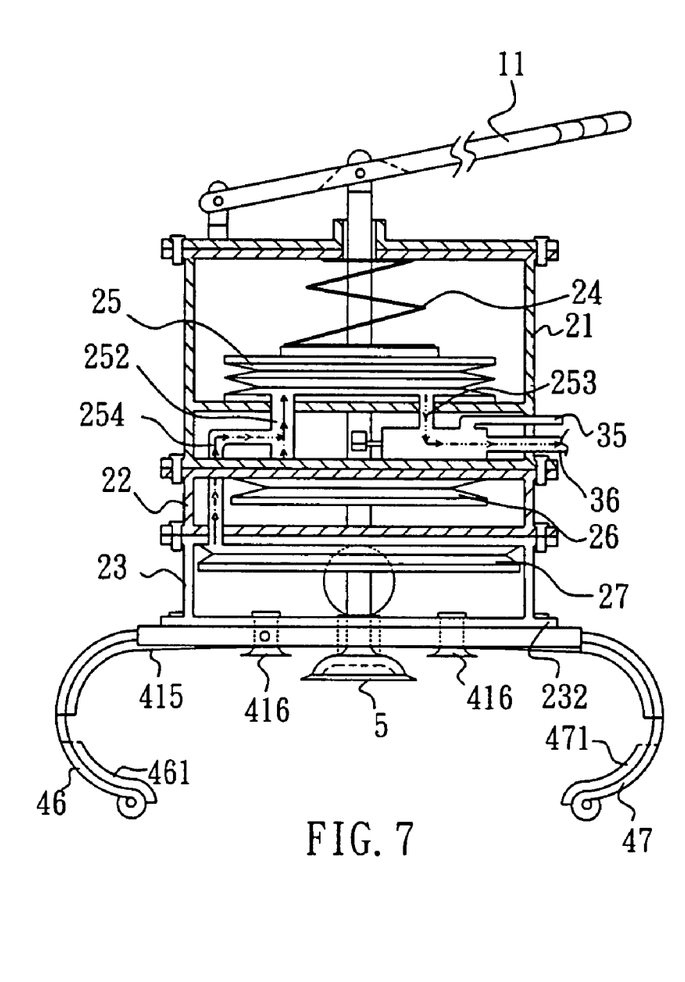
FIG. 7 is a sectional view with fragmentary side view illustrating the air storage device of the present invention discharging air.
Figure 8:
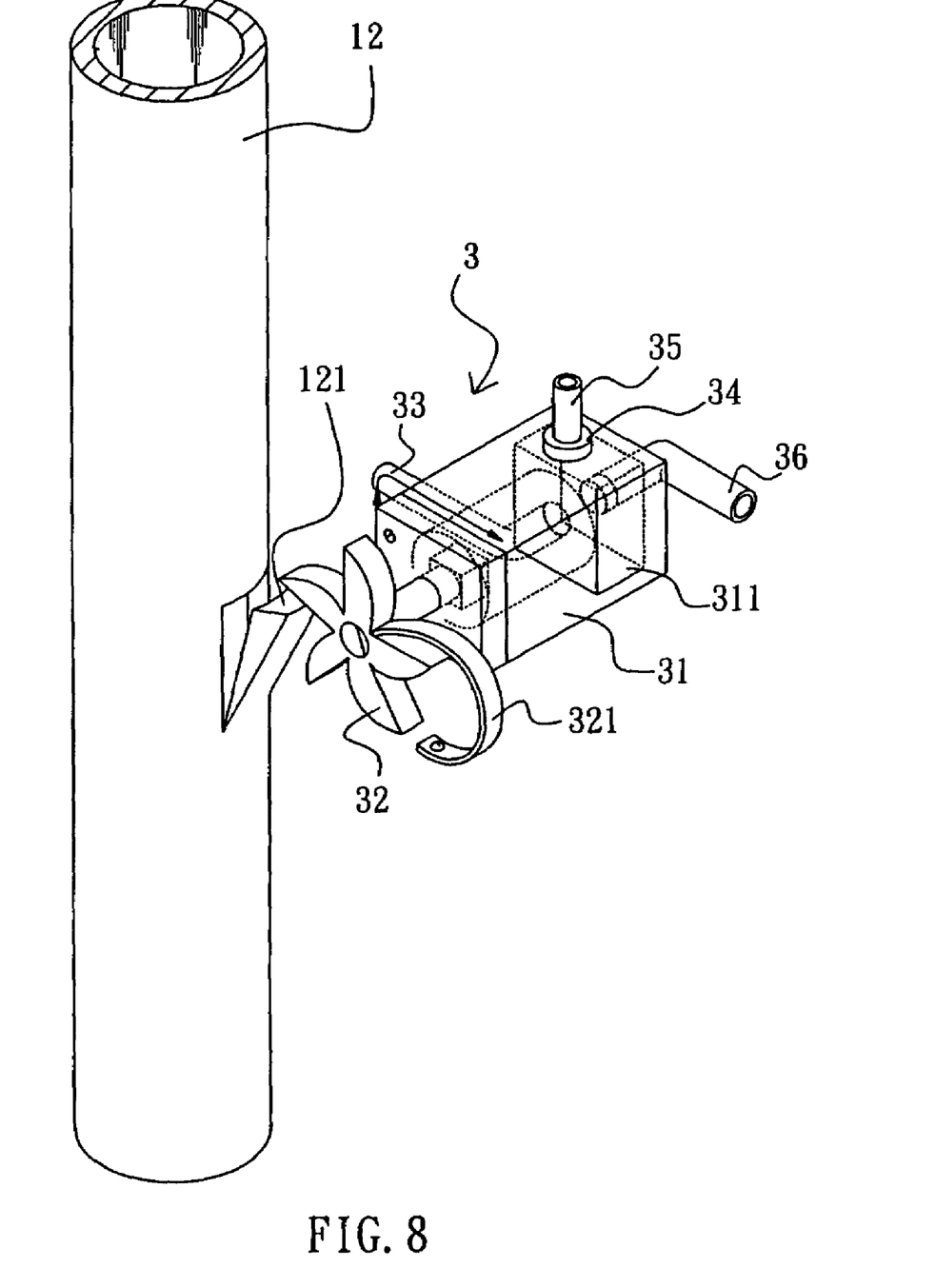
FIG. 8 is a perspective view illustrating the press lever with a push block pressing gears on the air control valve.
Figure 9:
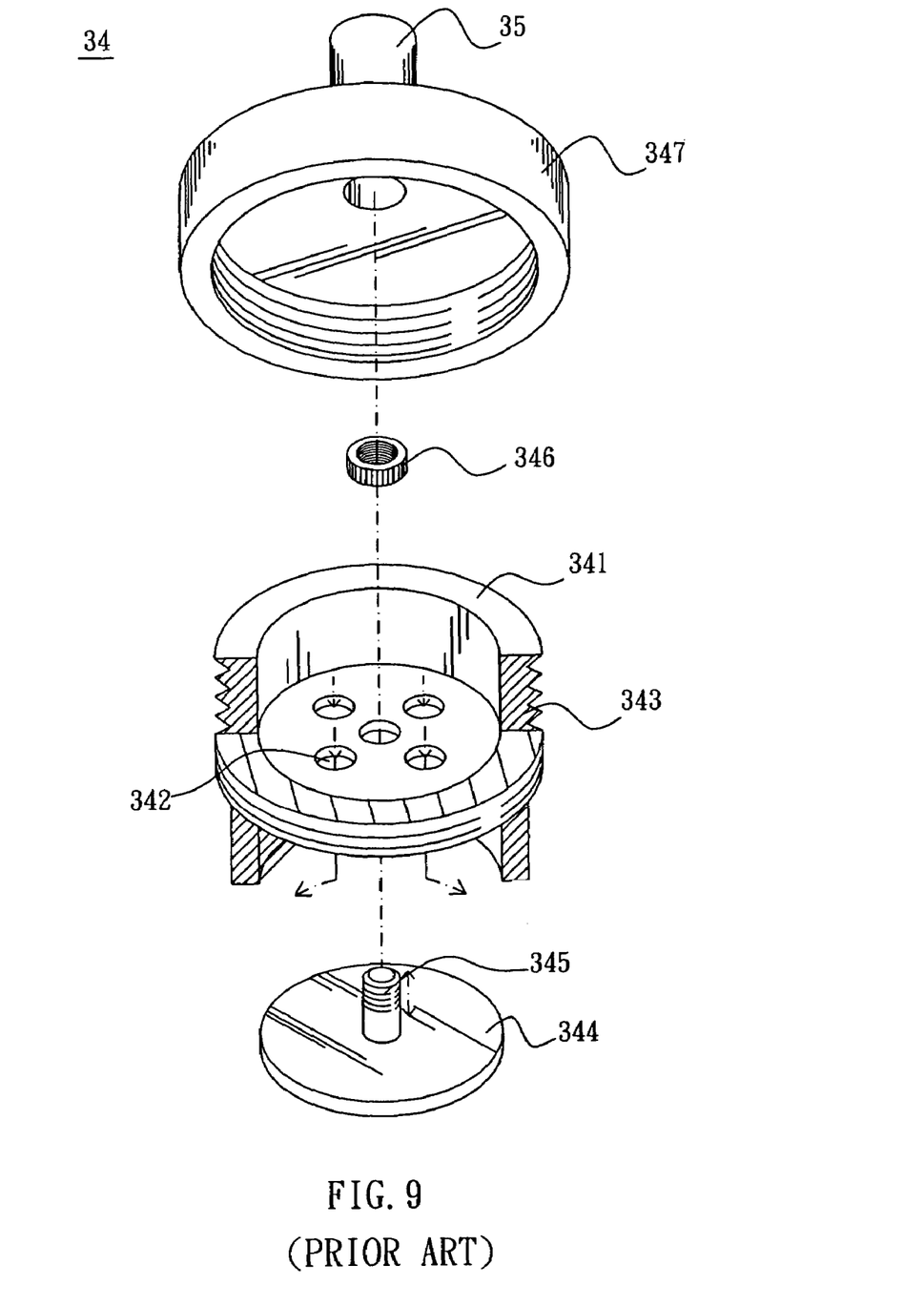
FIG. 9 is FIG. 7 of U.S. Pat. No. 6,397,843.

Referring to FIGS. 6 to 9, the control device 3 is disposed between the partition 213 and the bottom plate 212 in the first cylindrical member 21 and includes an air control valve 21 as shown in FIG. 8. The air control valve 31 is joined to a gear 32 at the lateral side thereof. A retaining plate 321 withstands against the gear 32 to avoid the gear 32 turning inversely and the gear 32 is pushed to rotate with the push piece 121 of the actuating piece 121. When the push piece 121 pushes the gear 32 five times, the air control valve 31 admits the air via the third intake pipe 33 and flowing toward an air control valve 31. The air control valve 31 is ioined to the first discharge pipe 253 to communicate with each other. The unidirectional valve 34 stops the air flowing outward via the fourth intake pipe 35. The air enters a mixing chamber 311 to mix with oxygen from the unidirectional valve 34 and the mixture flows outward via the second discharge pipe 36. The art of this part is the same as the air control valve disclosed in U.S. Pat. No. 6,397,843.

Referring to FIG. 9 again, the unidirectional air-guiding valve 34 includes a valve body 341 with a plurality of lower air opening 342 and outer threads 342, a screw rod 345 with a valve diaphragm 344, which passes through the central hole thereof engages with a nut 346, a cap 347 engaging with outer side of the valve body 341. The art of this part is the same as the unidirectional valve disclosed in U.S. Pat. No. 8,397,843.

Figure 10:
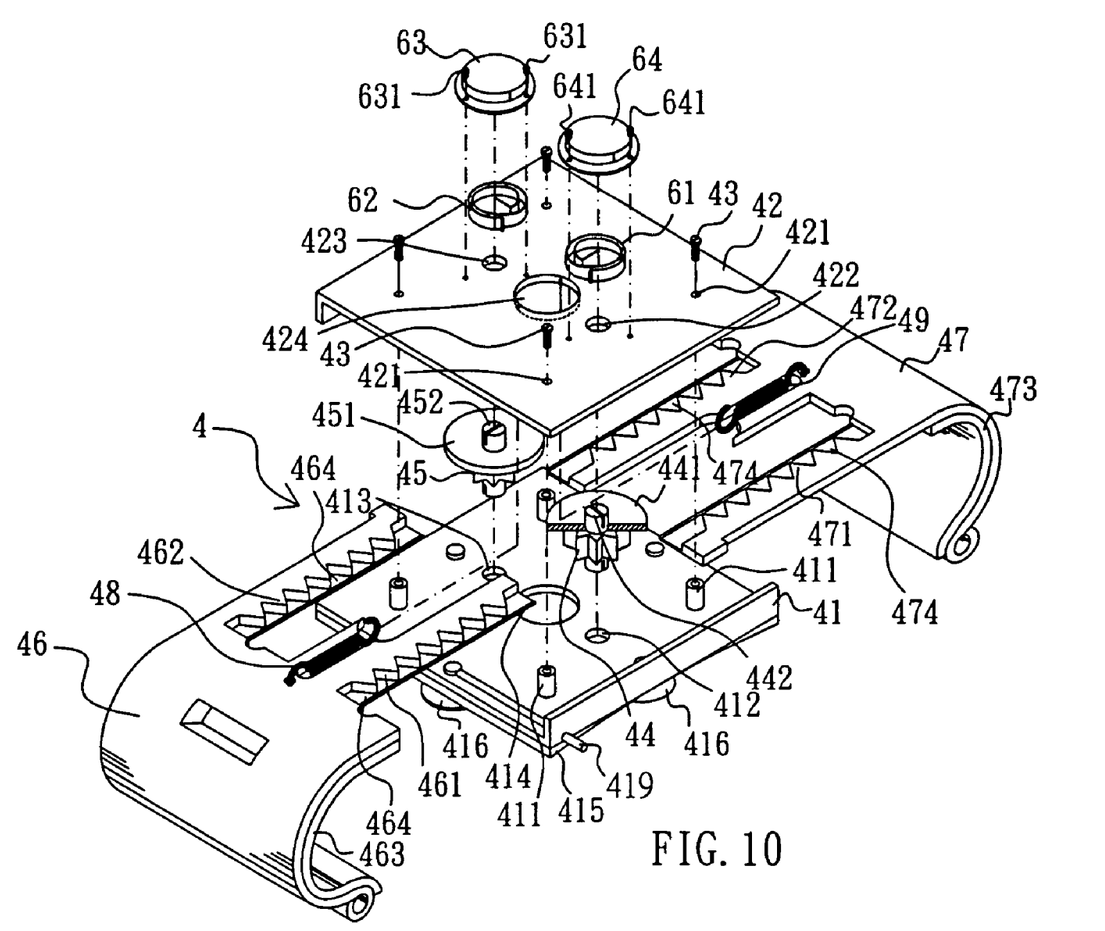
FIG. 10 is an exploded perspective view of the tying device of the present invention.

Referring to FIG. 10, the binding device 4 is attached to the lower end of the air storage device 2. The binding device 4 includes a bottom plate 41 and a cover plate 42 joined to the bottom plate 41. The bottom plate 41 has a plurality of pins 411 at the upper side thereof and each of the pins 411 provides a screw thread hole. The cover plate 42 has a plurality of holes 421 corresponding to the screw thread hole in each of the pins 411 respectively. A plurality of screws 43 pass through the holes 421 and engage with the screw thread holes in the pins 411 such that the cover plate 42 can be joined to the bottom plate 41.

The bottom plate 41 and the cover plate 42 each provide two holes (412, 413), (422, 423) and a central hole (414, 424) corresponding to each other. Two gears 44, 45 have a guard plate 441 at the upper sides thereof respectively. Two pull plates 46, 47 have two racks (461, 462), (471, 472). Four racks 461, 462, 471, 472 have a guard plate 464, 464, 474, 474 at the lower sides thereof respectively. The out side of the guard plates 464, 464, 474, 474 is bent upward respectively. The two racks 461, 471 mesh with two sides of the gear 44 and the guard plates 441, 464, 474 screen areas of the racks 461, 471 meshing with the gear 44. The two racks 462, 472 mesh with two sides of the gear 45 and the two guard plates 451, 464, 474 screen areas of the racks 462, 472 meshing with the gear 45. Two springs 48, 49 have two ends thereof being joined to the pull plates 46, 47 and two sides of the inner wall in the central hole of the cover plate 42.

Both ends of shafts of the gears 44, 45 movably fit with the corresponding holes 412, 422, 413, 423 of the bottom plate 41 and the cover plate 42 respectively. Upper ends 442, 452 of the shafts are joined to the inner end of a spiral springs 61, 62 respectively and the outer ends of the two spiral springs 61, 62 are joined to inner sides of two covers 63, 64 respectively. The covers 63, 64 are secured to the cover plate 42 with a plurality of screws 631, 641.

Figure 12:
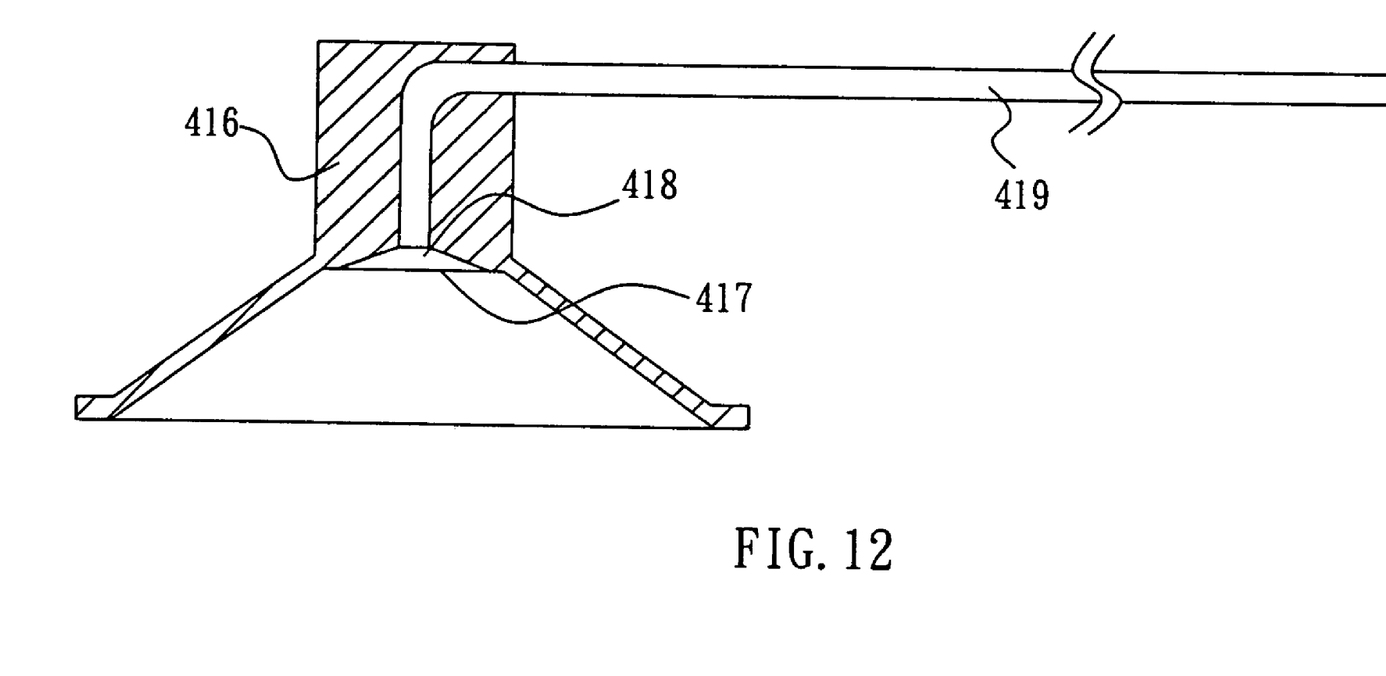
FIG. 12 is a sectional view illustrating a secure sucking disc connected to the voice guiding pipe.

Pads 415, 463, 473, which are made of soft material, are attached to bottom sides of the bottom plate 41 and the pull plates 46, 47 thereof. Outer ends of the pull plates 46, 47 with the soft pads 415 provide a curved shape for accommodating chest part of the human body. Four sides of the bottom plate 41 at the bottom side thereof is attached with a sucking disc 416 respectively. The sucking disc 416, which is disposed near the heart of a patient, has a diaphragm 417 inside as shown in FIG. 12. The diaphragm 417 has an upper hollow part 418. A sound guiding pipe 419 connects with the hollow part 418 for transmitting sound wave sent with the diaphragm 417 and extends outward the bottom plate 41 as shown in FIG. 10. The pull plates 46, 47 are mounted between the bottom plate 41 and the cover plate 42 and are in a state of unused state due to elastic forces of the springs 48, 49 and the spiral springs 61, 62 as shown in FIGS. 6 and 7. While in use, the pull plates 46, 47 are pulled outward and both lateral sides of the chest part of the patient can be bound by the pull plates 46, 47 rapidly due to the elastic forces of the springs 48, 49 and the spiral springs 61, 62 as shown in FIG. 11. The sucking discs can be arranged to place at press spots of the notch between the rib bones and the chest bones with the aid of observing through the peephole 233 of the third cylindrical member 23.

Referring to FIG. 11, the fixing plate 13 is attached with a bubble lever gage 133 and a sleeve 71 at the upper side thereof and the sleeve 71 receives a high-pressure oxygen vessel 72. The high-pressure vessel 72 has a switching push button 721 and connects with an end of an air-guiding pipe 722. Another end of the air-guiding pipe 722 connects with the fourth intake pipe 35. When the push button 721 is pressed down, the oxygen rushes into the fourth intake pipe 35. The second discharge pipe 36 connects with an end of a pressing ball 37 and another end of the pressing ball 37 connects with an end of the air passage pipe 9' shown in FIG. 1. Another end of the air passage pipe 9' connects with the mouth-nose breather 8' and the mouth-nose breather 8' masks the mouth and nose of the patient. The sound guiding pipe 419 connects with a stethoscope 96 such that the cardiopulmonary resuscitation can be operated.

Referring to FIGS. 6, 7, 8 and 11, once the user presses down the hand press lever 11, the actuating rod 12 can drive the second extendable air pump 26 and the third extendable air pump 27 to extend downward and expand the volumes thereof. At this time, the outside air can open the unidirectional valves 261, 271 to enter the second extendable air pump 26 and the third extendable air pump 27 as shown in FIG. 6. When the user raises the hand press lever 11, the actuating rod 12 drives the second extendable air pump 26 and the third extendable air pump 27 to reduce the volumes thereof. Right at the time, the unidirectional valves 261, 271 close respectively and the air in the second extendable air pump 26 and the third extendable air pump 27 is compressed to flow toward the first intake pipe 252 and the second intake pipe 254. The air in the second intake pipe 254 further flows into the first intake pipe 252. Right at the moment, the air pushes through the unidirectional valve 255 to enter the first extendable air pump 25 and the first extendable air pump 25 extends to compress the compression spring 24. Meanwhile, the push piece 121 of the actuating rod 12 drives one of the teeth on the gear 32 to move upward shown in FIG. 8. The air in the first extendable air pump 26 is incapable of being sent out via the first discharge pipe 253 due to being controlled by the control valve 31. Hence, every time the hand press lever 11 is pressed down, the sucking disc 5 under the actuating rod 12 presses the pressing spot once and every time the hand press lever 11 is raised, the air can be filled into the first extendable air pump 25. In case of the patient being pressed five times before the hand press lever 11 is raised, the gear 32 can be driven to rotate a revolution and to turn on the control valve 31 such that the first extendable air pump 25 can be compressed by way of the elastic force of the compression spring 24 and the air in the first extendable air pump 25 can enter the mixing chamber 311 to mix with the oxygen from the fourth intake pipe 35. Further, the mixed air can be blown into the mouth of the patient via the air passage pipe 9' and the mouth-nose breather 8'.

It is noted that the third cylindrical member 23 and the parts therein can be omitted and the second cylindrical member 22 can be joined to the binding device 40 directly. But, two extendable air pumps are utilized can obtain greater amount of filled air.

The invention can perform a procedure of pressing the pressed spot of the patient consecutive five times and admitting air automatically one time to make operation of the cardiopulmonary resuscitation more successfully and conveniently.

The part in mouth-nose breather, which has to contact with the mouth and nose of the patient, can be designed as a disposal part to avoid possible bacteria being infected between the patients.

The invention provides advantages such as the hand pressing filling the a great deal of air, a constant pressing force being obtained to press the heart, the sucking disc fixing to the pressed spot fast, breathing of the patient being capable of being checked with the bubble level gage, hart beating of the patient being capable of being checked with the stethoscope, the mixing chamber in the control valve being capable of mixing the oxygen and the air for increasing the content of oxygen in the air and the pressing ball being capable of supplementing oxygen or fresh air after heart restoring beating.

Furthermore, functions of the present invention such as the patient being bound conveniently, providing simple structure, being fabricated easily, supplying more air filled, supplying the patient sufficient blowing air are not provided in the preceding cited US patents.

While the invention has been described with referencing to a preferred embodiment thereof, it is to be understood that modifications or variations may be easily made without departing from the spirit of this invention, which is defined by the appended claims.

What is claimed is:

1. A hand press type rapid positioning first-aid device with cardiopulmonary resuscitation, comprising:
   a press device, further comprising a fixing plate, providing a fulcrum stem and having a central through hole; a hand press lever with two ends, one of the ends pivotally connecting with the fulcrum stem and the other one of the ends being free; an actuating rod, penetrating the through hole of the fixing plate, having a push piece on the outer wall surface thereof and being driven with the hand press lever; and a sucking disc, being joined to a lower end of the actuating rod;
   an air storage device, being mounted under the press device, sequentially joining with a first cylindrical member, at an least additional cylindrical member, a first intake pipe, a first discharge pipe and at least an additional intake pipe; wherein, the first cylindrical member further comprises a first top plate, having a through hole being penetrated with the actuating rod; a first bottom plate, having a through hole being penetrated with the actuating rod; a partition, being disposed between the first top plate and the first bottom plate, having a through hole being penetrated with the actuating rod and having another communicating hole corresponding to the communicating hole at the top plate; a first extendable air pump with an upper end and a lower end, having a central through hole being penetrated with the actuating rod, providing communicating holes; a compression spring with two ends, one of the ends being joined to the first top plate and the other one of the ends being joined to the upper end of the first extendable air pump; the at least an additional cylindrical member further comprises a top plate, providing a further communicating hole; at least an additional extendable air pump, providing a through hole being penetrated with the actuating rod, being airtightly joined to the outer wall surface of the actuating rod at the bottom thereof, being driven by the actuating rod to perform extendable movement and being attached with a unidirectional valve at the bottom thereof; the first intake pipe, being air-tightly joined to a communicating hole disposed at the top plate; the first discharge pipe, being air-tightly joined to a communicating hole at the partition of the first cylindrical member; and the at least an additional intake pipe, being air-tightly joined to a further communicating hole at the first bottom plate of the first cylindrical member and a further communicating hole at the top plate of the at least an additional cylindrical member respectively at the lower end thereof and being joined to another unidirectional valve at the upper end thereof;

a control device, being mounted between the partition and the first bottom plate, further comprises a control valve, providing a mixing chamber therein; a gear, being movably attached to a lateral side of the control valve, withstanding against a retaining plate to avoid turning inversely, being pushed to rotate with the push piece on the actuating piece; a further discharge pipe, being attached to the mixing chamber; a communicating pipe, being connected to the further discharge pipe at an end thereof and being connected to a mouth-nose breather; whereby, when the gear is pushed with the push piece five times, the control valve admits air to enter the mixing chamber and moving outward via the further discharge pipe such that the air can supply to the mouth and the nose of a patient; and a binding device, which is mounted under the air storage device, further comprising a lower plate, having a central hole and two other holes; a cover plate, having a central hole and two other holes corresponding to the holes of the lower plate; two additional gears, having a shaft respectively with both ends thereof movably fitting with the holes at the lower plate and the cover plate; two spiral springs with an inner end and an outer end respectively, the inner end being attached to the shaft, which is disposed over the other shaft; two covers, being joined to the upper side of the cover plate with the inner sides thereof being attached to the outer ends of the spiral springs; two pull plates, providing two racks meshing with the lateral sides of the two additional gears; whereby, the two pull plates can bind two lateral sides of the patient by way of elastic forces of the spiral springs after the pull plates are pulled outward.

2. The hand press type rapid positioning first-aid device with cardiopulmonary resuscitation as defined in claim 1, wherein the at least an additional cylindrical member comprises a second cylindrical member and a third cylindrical member, which is sequentially joined to the second cylindrical member, wherein the top plates of the second cylindrical member and the third cylindrical member are joined to a second extendable air pump and a third extendable air pump respectively at the inner sides thereof; the bottom plate of first cylindrical member and the top plate of the second cylindrical member have a hole respectively corresponding to each other to air-tightly join with a lower end of the first intake pipe and connect with a second intake pipe; the bottom plate of the second cylindrical member and the top plate of the third cylindrical member have a hole respectively corresponding to each other to air-tightly join with a lower end of the second intake pipe and an upper end of the second intake pipe connects with the lower end of the first intake pipe.

3. The hand press type rapid positioning first-aid device with cardiopulmonary resuscitation as defined in claim 1, wherein the central holes of the pull plates and the cover plate are attached with two ends of a spring at two sides of the inner walls thereof.

4. The hand press type rapid positioning first-aid device with cardiopulmonary resuscitation as defined in claim 1, wherein a guard plate is disposed at an upper side of the two additional gears respectively and a guard plate is disposed at the lower side of the four racks respectively to screen spots where the racks mesh with the gears.

5. The hand press type rapid positioning first-aid device with cardiopulmonary resuscitation as defined in claim 1, wherein the lower plate and the pull plates are attached with a soft pad respectively at the bottom sides thereof; the pads have a curved shape at the lower sides thereof respectively to accommodate the chest part of human body.

6. The hand press type rapid positioning first-aid device with cardiopulmonary resuscitation as defined in claim 1, wherein the lower plate provides a sucking disc at four sides of the lower side thereof.

7. The hand press type rapid positioning first-aid device with cardiopulmonary resuscitation as defined in claim 6, wherein at least one of the sucking disc being disposed near the heart of a patient provides an inner diaphragm and a hollow part above the diaphragm; a sound guiding pipe communicates with the hollow part for transmitting sound wave sent by the diaphragm and extends outward the lower plate.

8. The hand press type rapid positioning first-aid device with cardiopulmonary resuscitation as defined in claim 7, wherein the sound guiding pipe connects with a stethoscope.

9. The hand press type rapid positioning first-aid device with cardiopulmonary resuscitation as defined in claim 1, wherein the at least an additional cylindrical member, which is disposed at the lowest position, provides at least an observation hole at a circumferential wall thereof.

10. The hand press type rapid positioning first-aid device with cardiopulmonary resuscitation as defined in claim 1, wherein the mixing chamber is associated with a unidirectional air-guiding valve and the unidirectional air-guiding valve connects with the at least an additional intake pipe to admit air coming from the at least an additional intake pipe.

11. The hand press type rapid positioning first-aid device with cardiopulmonary resuscitation as defined in claim 10, wherein the unidirectional air-guiding valve comprises a valve body with a plurality of lower air opening and outer screw threads, a screw rod with a valve diaphragm, which passes through the central hole thereof to engage with a nut, a cap engaging with outer side of the valve body.

12. The hand press type rapid positioning first-aid device with cardiopulmonary resuscitation as defined in claim 10, wherein the fixing plate is attached with a bubble lever gage and a sleeve at the upper side thereof and the sleeve receives a high-pressure oxygen vessel with an end of the high-pressure vessel connecting with an end of an air-guiding pipe and another end of the air-guiding pipe connecting with a further intake pipe.

13. The hand press type rapid positioning first-aid device with cardiopulmonary resuscitation as defined in claim 1, wherein the fixing plate is joined with a bubble level gage at the upper side thereof.

14. The hand press type rapid positioning first-aid device with cardiopulmonary resuscitation as defined in claim 1, wherein a pressing ball is disposed between the discharge pipe and the communicating pipe of the mixing chamber.

15. The hand press type rapid positioning first-aid device with cardiopulmonary resuscitation as defined in claim 1, wherein the mouth-nose breather is attached to the mouth and nose of the patient and comprises a hose, a coupling sleeve, an air-turning baffler, a sleeve, a two-way valve, a nostril breather, a nostril three-way pipe, a hollow mask, a mouth holder and a belt; an end of an air duct connects with the air control valve and the air-turning baffler is connected to another end of the air duct; the two-way valve has a cylindrical shape, which is made of elastic material and received in the air-turning baffler, with a conical end; the nostril breather has a central air guide pipe and a plurality of apertures at the periphery thereof with a side thereof facing the air-turning baffler; the nostril three-way pipe provides two holes at an end thereof to communicate with the nose of the patient and has a single hole at another end thereof for communicating with the air guide pipe of the nostril breather; the sleeve connects with the air-turning baffler at an end thereof and connects with a mouth holder; another end of the mouth holder is placed at the inner side of the mouth; an end of the hose is inserted into the mouth and joined to the mouth holder and another end of the hose is connected to the air turning baffler; and the hollow mask provides a shape accommodating with the mouth for preventing the mouth holder or the hose from being inserted too deep into the mouth.

* * * * *